US008262990B2

(12) United States Patent
Bair et al.

(10) Patent No.: US 8,262,990 B2
(45) Date of Patent: *Sep. 11, 2012

(54) FLOW CYTOMETER SYSTEM WITH UNCLOGGING FEATURE

(75) Inventors: Nathaniel C. Bair, Ann Arbor, MI (US); Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 102 days.

This patent is subject to a terminal disclaimer.

(21) Appl. No.: 12/857,405

(22) Filed: Aug. 16, 2010

(65) Prior Publication Data
US 2010/0319786 A1    Dec. 23, 2010

Related U.S. Application Data

(63) Continuation of application No. 11/735,456, filed on Apr. 14, 2007, now Pat. No. 7,780,916, which is a continuation-in-part of application No. 11/370,714, filed on Mar. 8, 2006, now Pat. No. 8,017,402.

(60) Provisional application No. 60/792,536, filed on Apr. 17, 2006.

(51) Int. Cl.
*G01N 21/00* (2006.01)
*B08B 7/00* (2006.01)
*F17D 1/00* (2006.01)
*G01N 35/08* (2006.01)

(52) U.S. Cl. ............. 422/62; 422/67; 422/68.1; 422/81; 422/500; 422/501; 137/7; 137/12; 137/15.01; 137/565.11; 436/50; 436/52

(58) Field of Classification Search ........................ None
See application file for complete search history.

(56) References Cited

U.S. PATENT DOCUMENTS

| | | | |
|---|---|---|---|
| 3,347,273 A | 10/1967 | Russell |
| 3,061,128 A | 12/1968 | Hakim |
| 3,672,402 A | 6/1972 | Bloemer |
| 4,112,735 A | 9/1978 | McKnight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |

(Continued)

FOREIGN PATENT DOCUMENTS
EP              466490 A     1/1992
(Continued)

*Primary Examiner* — Neil N Turk
(74) *Attorney, Agent, or Firm* — Jeffrey Schox

(57) ABSTRACT

The fluidic system with an unclogging feature of the preferred embodiment includes a flow channel, a sheath pump to pump sheath fluid from a sheath container into an interrogation zone, and a waste pump to pump waste fluid from the interrogation zone into a waste container. The sheath pump and/or the waste pump draw sample fluid from a sample container into the interrogation zone. The fluidic system also includes a controller to adjust the flow rate of the sample fluid from the sample container into the interrogation zone. The pump and controller cooperate to propagate a pulsation through the flow channel from the pump if the flow channel is clogged. The fluidic system is preferably incorporated into a flow cytometer with a flow cell that includes the interrogation zone.

22 Claims, 1 Drawing Sheet

U.S. PATENT DOCUMENTS

| | | |
|---|---|---|
| 4,755,021 A | 7/1988 | Dyott |
| 4,790,653 A | 12/1988 | North, Jr. |
| 4,818,103 A | 4/1989 | Thomas et al. |
| 4,824,641 A | 4/1989 | Williams |
| 4,826,660 A | 5/1989 | Smith et al. |
| 4,844,610 A | 7/1989 | North, Jr. |
| 4,933,813 A | 6/1990 | Berger |
| 5,028,127 A | 7/1991 | Spitzberg |
| 5,040,890 A | 8/1991 | North, Jr. |
| 5,043,706 A | 8/1991 | Oliver |
| 5,083,862 A | 1/1992 | Rusnak |
| 5,138,868 A | 8/1992 | Long |
| 5,139,609 A | 8/1992 | Fields et al. |
| 5,150,037 A | 9/1992 | Kouzuki |
| 5,150,313 A | 9/1992 | Van Den et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 | 7/2003 | Colon |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich |
| 7,362,432 B2 | 4/2008 | Roth |
| 7,403,125 B2 | 7/2008 | Rich |
| 7,471,393 B2 | 12/2008 | Trainer |
| 7,520,300 B2 | 4/2009 | Rich |
| 7,628,956 B2 | 12/2009 | Jindo |
| 7,738,099 B2 | 6/2010 | Morrell et al. |
| 7,739,060 B2 | 6/2010 | Goebel et al. |
| 7,776,268 B2 | 8/2010 | Rich |
| 7,780,916 B2 | 8/2010 | Bair et al. |
| 7,843,561 B2 | 11/2010 | Rich |
| 7,857,005 B2 | 12/2010 | Rich et al. |
| 7,981,661 B2 | 7/2011 | Rich |
| 7,996,188 B2 | 8/2011 | Olson et al. |
| 8,017,402 B2 | 9/2011 | Rich |
| 8,031,340 B2 | 10/2011 | Rich et al. |
| 2001/0014477 A1* | 8/2001 | Pelc et al. .................. 436/49 |
| 2001/0039053 A1 | 11/2001 | Liseo et al. |
| 2002/0028434 A1 | 3/2002 | Goix et al. |
| 2002/0049782 A1 | 4/2002 | Herzenberg et al. |
| 2002/0059959 A1 | 5/2002 | Qatu et al. |
| 2002/0080341 A1 | 6/2002 | Kosaka |
| 2002/0123154 A1 | 9/2002 | Burshteyn et al. |
| 2002/0192113 A1* | 12/2002 | Uffenheimer et al. .......... 422/67 |
| 2003/0035168 A1 | 2/2003 | Qian et al. |
| 2003/0048539 A1 | 3/2003 | Oostman et al. |
| 2003/0054558 A1 | 3/2003 | Kurabayashi et al. |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0175157 A1 | 9/2003 | Micklash, II et al. |
| 2003/0202175 A1 | 10/2003 | Van Den et al. |
| 2003/0211009 A1 | 11/2003 | Buchanan |
| 2003/0223061 A1 | 12/2003 | Sebok et al. |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0201845 A1 | 10/2004 | Quist et al. |
| 2004/0246476 A1 | 12/2004 | Bevis et al. |
| 2005/0044110 A1 | 2/2005 | Herzenberg et al. |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |

| | | |
|---|---|---|
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber et al. |
| 2006/0177937 A1 | 8/2006 | Kurabayashi et al. |
| 2006/0219873 A1 | 10/2006 | Martin et al. |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |
| 2007/0096039 A1 | 5/2007 | Kapoor et al. |
| 2007/0124089 A1 | 5/2007 | Jochum et al. |
| 2007/0127863 A1 | 6/2007 | Bair et al. |
| 2007/0144277 A1 | 6/2007 | Padmanabhan et al. |
| 2007/0212262 A1 | 9/2007 | Rich |
| 2007/0224684 A1 | 9/2007 | Olson et al. |
| 2007/0243106 A1 | 10/2007 | Rich |
| 2008/0055595 A1 | 3/2008 | Olson et al. |
| 2008/0064113 A1 | 3/2008 | Goix et al. |
| 2008/0092961 A1 | 4/2008 | Bair et al. |
| 2008/0152542 A1 | 6/2008 | Ball et al. |
| 2008/0215297 A1 | 9/2008 | Goebel et al. |
| 2008/0228444 A1 | 9/2008 | Olson et al. |
| 2009/0104075 A1 | 4/2009 | Rich |
| 2009/0174881 A1 | 7/2009 | Rich |
| 2009/0201501 A1 | 8/2009 | Bair et al. |
| 2009/0202130 A1 | 8/2009 | George et al. |
| 2009/0216478 A1 | 8/2009 | Estevez-Labori |
| 2009/0260701 A1 | 10/2009 | Rich |
| 2009/0293910 A1 | 12/2009 | Ball et al. |
| 2010/0012853 A1 | 1/2010 | Parks et al. |
| 2010/0032584 A1 | 2/2010 | Dayong et al. |
| 2010/0118298 A1 | 5/2010 | Bair et al. |
| 2010/0119298 A1 | 5/2010 | Huang |
| 2010/0302536 A1 | 12/2010 | Ball et al. |
| 2010/0319469 A1 | 12/2010 | Rich |
| 2011/0008816 A1 | 1/2011 | Ball et al. |
| 2011/0058163 A1 | 3/2011 | Rich |
| 2011/0061471 A1 | 3/2011 | Rich et al. |
| 2011/0306031 A1 | 12/2011 | Rich |

FOREIGN PATENT DOCUMENTS

| | | |
|---|---|---|
| EP | 1391611 A | 2/2004 |
| EP | 1396736 A | 3/2004 |
| EP | 1521076 A | 4/2005 |
| JP | 356169978 | 12/1981 |
| JP | 04086546 H | 3/1992 |
| JP | 6194299 A | 7/1994 |
| JP | 06221988 H | 12/1994 |
| JP | 7260084 A | 10/1995 |
| JP | 08201267 H | 8/1996 |
| JP | 09288053 H | 11/1997 |
| JP | 10227737 | 8/1998 |
| JP | 2001050887 A | 2/2001 |
| JP | 2001170062 A | 6/2001 |
| JP | 2003262201 A | 9/2003 |
| JP | 200477484 | 3/2004 |
| WO | 9956052 | 11/1999 |
| WO | 0194914 | 12/2001 |
| WO | 2005017499 A | 2/2005 |
| WO | 2005068971 A | 7/2005 |
| WO | 2005073694 A | 8/2005 |
| WO | 2005091893 A | 10/2005 |
| WO | 2006055722 A | 5/2006 |
| WO | 2007067577 A | 6/2007 |
| WO | 2008/058217 | 7/2007 |
| WO | 2007100723 A | 9/2007 |
| WO | 2007103969 A | 9/2007 |
| WO | 2007136749 A | 11/2007 |
| WO | 2010101623 A | 9/2010 |

* cited by examiner

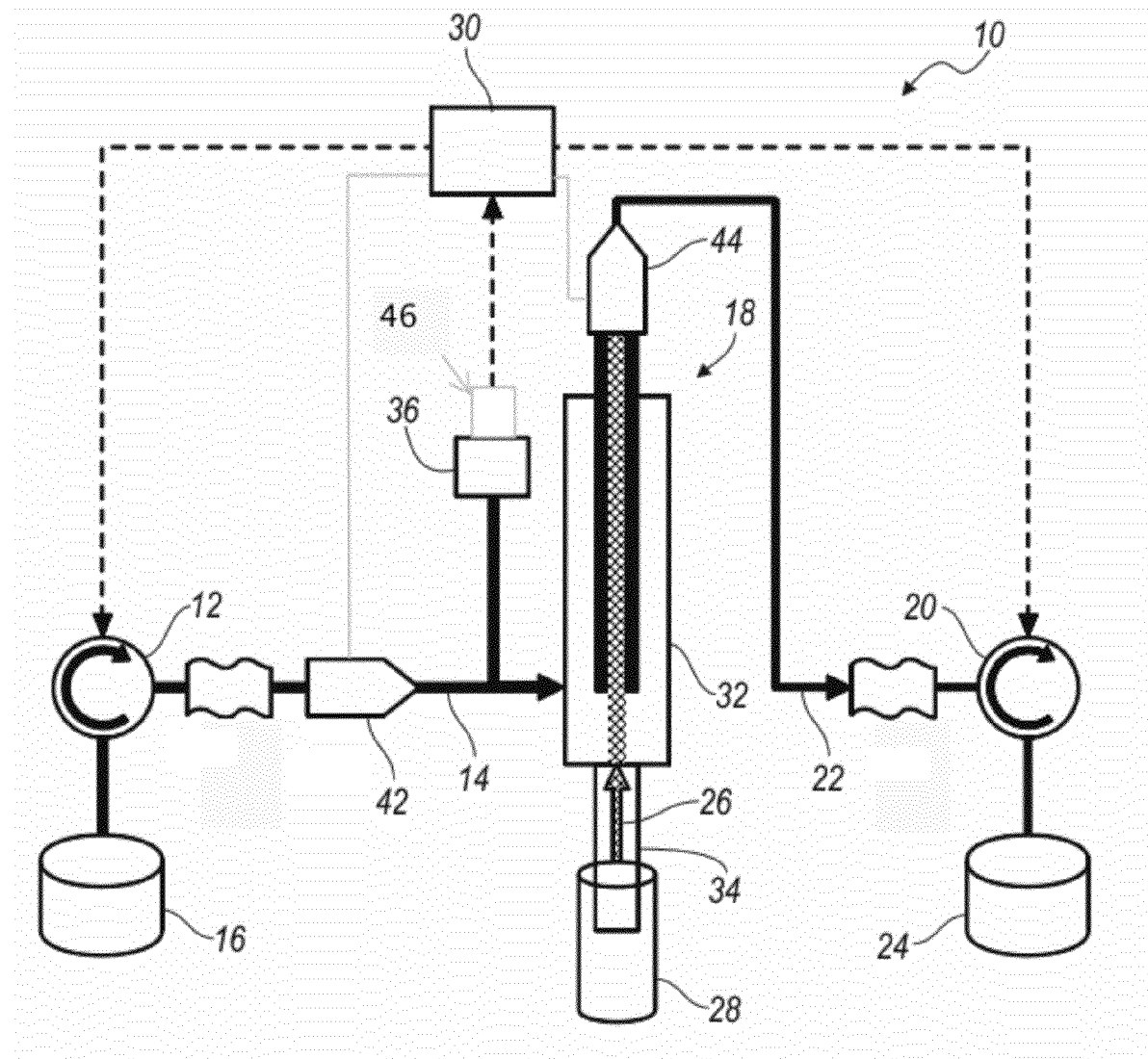

FLOW CYTOMETER SYSTEM WITH UNCLOGGING FEATURE

CROSS-REFERENCE TO RELATED APPLICATIONS

This application is a continuation of U.S. application Ser. No. 11/735,456, filed 14 Apr. 2007 and entitled "Flow Cytometer System With Unclogging Feature", which is a Continuation-in-Part of U.S. application Ser. No. 11/370,714, filed on 8 Mar. 2006 and entitled "Fluidic System for a Flow Cytometer" and claims the benefit of U.S. Provisional Application No. 60/792,536, filed 17 Apr. 2006 and entitled "Flow Cytometer System with Unclogging Feature". All of these applications are incorporated in their entirety by this reference.

TECHNICAL FIELD

This invention relates generally to the flow cytometer field, and more specifically to an improved fluidic system with an unclogging feature in the flow cytometer field.

BACKGROUND

Typical flow cytometer systems require a very small flow channel, typically less than 0.3 mm in diameter, through which cells or other particles flow in order to be counted. It is not uncommon for the small flow channels to become clogged by debris or clusters of cells. Typically, a clogged flow channel requires the user to halt operation of the flow cytometer system and manually unclog, backflush, clean, and/or replace the flow cell before proceeding. This process can take from minutes to hours and cause significant delay to experiments and inconvenience to the user.

Thus, there is a need for improved flow cytometer systems that minimize or avoid this delay or inconvenience. This invention provides such an improved and useful flow cytometer system.

BRIEF DESCRIPTION OF THE FIGURE

The FIGURE is a schematic representation of the fluidic system with an unclogging feature of the preferred embodiment of the invention.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

As shown in the FIGURE, the fluidic system 10 with an unclogging feature of the preferred embodiment includes a flow channel, a sheath pump 12 to pump sheath fluid 14 from a sheath container 16 into an interrogation zone 18 and a waste pump 20 to pump the sheath fluid 14 and a sample fluid 26 as waste fluid 22 from the interrogation zone 18 into a waste container 24. The sheath pump 12 and/or the waste pump 20 draw sample fluid 26 from a sample container 28 into the interrogation zone 18. The fluidic system 10 also includes a controller 30 to adjust the flow rate of the sample fluid 26 from the sample container 28 into the interrogation zone 18. At least one of the sheath pump 12 and waste pump 20 and the controller 30 cooperate to propagate a pulsation through the flow channel from the sheath pump 12 and/or waste pump 20 if the flow channel is clogged. The interrogation zone 18 functions to provide a location for the fluidic system 10 and an optical system of the flow cytometer to cooperatively facilitate the analysis of the sample fluid 26. The interrogation zone 18 is preferably enclosed within a removable flow cell 32, but may alternatively be defined by any suitable system or device. The fluidic system 10 is preferably incorporated into a flow cytometer, but may be alternatively incorporated into any suitable system that pumps a first fluid from a first container into an interrogation zone, draws a second fluid from a second container into the interrogation zone, and pumps the combined fluids from the interrogation zone into a third container.

The flow channel of the preferred embodiment is a very small passageway, typically less than 0.3 mm in diameter, through which cells and sample particles pass during, before, or after interrogation. The term flow channel as is used herein also refers to a flow tip, which is commonly used in the case of sorting flow cytometers. A clog in the flow channel may be the result of anything preventing or altering flow. A full blockage of the flow channel or a partial blockage of the flow channel may both be considered clogs of the flow channel. Examples of material that may clog the flow channel include sample debris, conjugated or clustered cells, or other substances inserted into the flow path of the flow cytometer. The sample may be anything capable of being inserted into the flow path. Samples may include cells, biological materials, or other particles to be assayed, measured, or counted. It should be understood that breaking up a clog in a flow channel includes both the full removal of a blockage from the flow channel as well as the loosening up or partial removal of a blockage from the flow channel, such that—with the addition of a fluid flow—the clog is substantially removed. It should further be understood that cleaning of a flow channel does not preclude the ability of the flow channel to be manually cleaned or manually unclogged.

The sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 within the flow cell 32 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system 10 is relatively easy to assemble, light to haul, quick to control, and easy to clean. Alternatively, the sheath pump 12 may be any suitable pump that pumps sheath fluid 14 from a sheath container 16 into an interrogation zone 18.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from a waste container 24 into an interrogation zone 18.

The sheath pump 12 and the waste pump 20 of the preferred embodiment cooperate to draw the sample fluid 26 from the sample container 28 and through a drawtube 34. The sample fluid 26 contains particles to be analyzed by the flow cytometer. The sample fluid 26 is preferably blood, but the sample fluid 26 may alternatively be any suitable fluid to be analyzed by the flow cytometer. The sample container 28, which functions to contain the sample fluid 26, is preferably an open beaker with a volume of approximately 5 mL, but may alternatively be any suitable container to contain the sample fluid 26. The drawtube 34, functions to convey the sample fluid 26 from the sample container 28 into the interrogation zone 18, is a conventional drawtube, but may alternatively be any suitable device to convey the sample fluid 26.

The sheath pump 12 and the waste pump 20 preferably cooperate to draw the sample fluid 26 from the sample container 28 into the interrogation zone 18 through the use of a pressure differential (e.g., the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. By varying the flow rates of the sheath pump 12 and the waste pump 20, the controller 30 can induce pulsations within the sheath fluid and the sample fluid. The controller 30 varies the flow rate of the fluids within the system such that each change of the flow rate is accompanied by a commensurate change in the fluid pressure within the system, thereby removing any clogs from the flow channel through these pulsations. Alternatively, the system may include other suitable controllable devices that draw the sample fluid from the sample container into the interrogation zone through the use of a pressure differential.

In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. The preferred controller 30 in this variation is coupled to the variable drive ratio device such that the controller 30 can vary the relative flow rates of the sheath pump 12 and the waste pump 20, wherein varying the pumping rates of the pumps of the system varies the flow rate of the system fluid, and each change of the flow rate of system fluid is accompanied by a commensurate change in the pressure within the system, thereby inducing pulsations in the system fluids at discrete or conditional intervals.

In a second and third variation, the fluidic system 10 of the preferred embodiment may also include a valve 42 located before the interrogation zone 18 and a valve 44 located after the interrogation zone 18. The valves 42 and 44 function to facilitate the control of the sheath fluid 14 and the waste fluid 22. The valves 42 and 44 are preferably check-valves, but may alternatively be any suitable valve to facilitate the control of the sheath fluid 14 and the waste fluid 22 such as by-pass valves, restrictive valves, and/or shutoff valves.

In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. The preferred controller 30 in this variation is coupled to the by-pass valve and adapted to divert a variable amount of fluid through the by-pass valve at discrete or conditional intervals in order to induce pulsations in the system fluids.

In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. The restrictive valve maybe a shutoff valve that alters the fluid flow and, therefore, allows for a variable flow rate of the sheath fluid and/or waste fluid. The preferred controller 30 in this variation is coupled to the restrictive valve and adapted to open/close the shutoff valve at discrete or conditional intervals in order to induce pulsations in the system fluids.

In a fourth variation, the sheath pump 12 and the waste pump 20 are driven by separate motors with separate controls and, therefore, allow for a variable flow rate of the sheath fluid 14 and/or waste fluid 22. The preferred controller 30 in this variation is coupled to one or both of the separate controls of the respective pumps, thereby permitting the controller 30 to induce pulsations in the system fluids at discrete or conditional intervals. The fluidic system 10 may, however, include other suitable variations that draw the sample fluid 26 from the sample container 28 into the interrogation zone 18 through the use of a pressure differential.

The controller 30 of the preferred embodiment functions to adjust the flow rate of the sample fluid 26 from the sample container 28 into the interrogation zone 18. The controller 30 of the preferred embodiment is connected to the sheath pump 12, the waste pump 20, and/or one or more valves positioned near the respective pumps. The controller 30 is adapted to create pulsations within the fluids through manipulations of the pumping rates of the respective pumps as well as the one or more valves. The controller 30 varies the flow rate of the fluids within the system such that each change of the flow rate is accompanied by a commensurate change in the fluid pressure within the system, thereby removing any clogs from the flow channel through these pulsations. The pressures of the pulsations created are preferably five or six times greater than the baseline pressures maintained in the flow channel, but may alternatively be any suitable pressure to remove any clogs from the flow channel.

Preferably, the controller 30 adjusts the flow rate of the sample fluid 26 by adjusting the variable flow rate of the sheath fluid 14 and/or the waste fluid 22. More preferably, the controller 30 adjusts the flow rate of the sample fluid 26 by allowing an adjustable flow rate of the sheath fluid 14 from the sheath container 16 to the interrogation zone 18, while maintaining a consistent flow rate of the waste fluid 22 from the interrogation zone 18 into the waste container 24. The advantage of this arrangement is a finer control of the flow rate of the sample fluid 26. Alternatively, the controller 30 may adjust the flow rate of waste fluid 22 while maintaining the flow rate of the sheath fluid 14, or may simultaneously adjust the flow rates of the sheath fluid 14 and the waste fluid 22. Furthermore, the controller 30 may employ one technique (such as allowing an adjustable flow rate of the sheath fluid 14, while maintaining a consistent flow rate of the waste fluid 22) in most situations, and may employ another technique (such as simultaneously adjusting the flow rates of the sheath fluid 14 and the waste fluid 22) in other situations to quickly response to a user input.

Control of the flow rate of the fluids within the system can be accomplished through variable pump rates for the respective pumps and/or variable opening or restriction of the one or more valves. Preferably, the controller 30 varies the flow rate at a discrete and repeatable interval, such as between one and ten times per second, creating pulsations with frequencies ranging from 1 Hz to 10 Hz. Alternatively, the controller 30 varies the flow rate at variable intervals, thus creating pulsations with variable frequencies within the system. The controller 30 may alternatively vary the flow rate at any other suitable interval or frequency. The controller 30 is preferably a proportional-integral-derivative (PID) controller, but may alternatively be a proportional-integral (PI) controller, a proportional-derivative (PD) controller, a proportional (P) controller, or any other suitable controller.

The controller 30 may create pulsations at conditional intervals in response to the presence of a clog in the flow channel. The presence of a clog may be detected by a user and signaled through a suitable input device, such as a switch. The presence of a clog may, however, be detected through automated means. Alternatively, rather than in response to the presence of a clog in the flow channel, the controller 30 may create pulsations in anticipation of a clog in the flow channel. Turning on the variable flow rate control in anticipation of a clog may be part of a regular maintenance or cleaning routine that serves to prevent a clog in the flow channel from forming.

The presence of a clog may be automatically detected. In a first variation, the controller 30 may be coupled to a clog detector 46 as shown in the FIGURE. The clog detector 46 functions to detect clogs in the flow channel, in response to which the controller 30 is adapted vary the flow rate of the fluids within the system to remove the clog. The clog detector 46 preferably includes either direct or indirect clog detection devices or methods. The clog detector 46 may alternatively include any suitable device or method.

In another variation, the fluidic system 10 can include a detector 36, which can include a pressure sensor or a flow meter. In a second variation, the fluidic system 10 of the preferred embodiment also includes a pressure sensor 36 that functions to measure a pressure of the sheath fluid 14 as close as possible to the inlet for the sample fluid 26. This measured pressure is an adequate estimate for the pressure of the sample fluid 26. The pressure sensor 36 preferably measures a pressure differential between the top of the drawtube 34 near the flow cell 32 and the bottom of the drawtube 34 near the sample container 28, but may alternatively measure a pressure differential between the drawtube 34 and atmosphere. The controller 30 is preferably connected to the pressure sensor 36 and adjusts the flow rate of the sample fluid 26 based on the measured pressure. The controller 30 may alternatively or additionally be connected to other suitable devices to assist in the control of the flow rate of the sample fluid 26. The pressure sensor 36 functions to detect clogs in the flow channel by detecting a change in pressure, in response to which the controller 30 is adapted to vary the flow rate of the fluids within the system to remove the clog. In a third variation, the fluidic system 10 may include a flow meter 36 that functions to measure the flow rate of the sample fluid 26 from the sample container 28 into the interrogation zone 18. The flow meter 36 functions to detect clogs in the flow channel by detecting a change in flow rate, in response to which the controller 30 is adapted to vary the flow rate of the fluids within the system to remove the clog.

The pulsations are preferably programmed to turn off when a user-defined or pre-defined parameter has been achieved. Examples of user-defined or pre-defined parameter include time interval, energy output, full or partial return of flow, break up of the clog, or a combination of the above. The process may, however, be fully automated such that the flow cytometer detects a clog, takes appropriate cleaning action, detects a successful unblocking, and then resumes the experiment, with minimal or no user intervention. An example of taking appropriate cleaning action includes suspending the sample flow or a cell count process and turning on the variable flow rate control. An example of resuming the experiment includes turning off the variable flow rate control and resuming sample flow or a cell count process. It is also possible that some clogs in the flow channel will be resistant to being broken up by the variable flow rate control of the preferred embodiment. In these cases, the flow cytometer system preferably signals the user to take appropriate action.

As a person skilled in the art of flow cytometers will recognize from the previous detailed description and from the figures and claims, modifications and changes can be made to the preferred embodiment of the invention without departing from the scope of this invention defined in the following claims.

We claim:

1. A fluidic system for unclogging a flow channel of a flow cytometer including an interrogation zone and a system fluid with a pressure and a flow rate, the fluidic system comprising:
    a sheath pump adapted to pump the system fluid from a sheath container into the interrogation zone;
    a waste pump adapted to pump the system fluid from the interrogation zone into a waste container;
    a motor with motor controls coupled to at least one of the pumps of the fluidic system;
    a clog detector that automatically detects clogs in the flow channel; and
    a controller connected to the motor and the clog detector and configured to vary the pumping rate of at least one of the pumps of the fluidic system to vary the flow rate of the system fluid and induce a commensurate change in the pressure of the system fluid to create pulsations within the system fluid in response to detection of a clog that provides to unclog the flow channel of the flow cytometer, wherein the controller is configured to create pulsations that have a pulsation pressure that is at least five time greater than the pressure of the system fluid.

2. The fluidic system of claim 1, wherein the pulsations have a time interval of separation equal to or less than one second.

3. The fluidic system of claim 1, wherein the clog detector comprises a pressure sensor that automatically detects clogs in the flow channel by measuring a pressure of the system fluid.

4. A fluidic system for unclogging a flow channel of a flow cytometer including an interrogation zone and a system fluid with a pressure and a flow rate, the fluidic system comprising:
    a sheath pump adapted to pump the system fluid from a sheath container into the interrogation zone;
    a waste pump adapted to pump the system fluid from the interrogation zone into a waste container;
    a motor with motor controls coupled to at least one of the pumps of the fluidic system;

a drawtube that conveys a sample fluid from a sample container into the interrogation zone;

a pressure sensor that automatically detects clogs in the flow channel by measuring a pressure of the system fluid, wherein the pressure sensor measures a pressure differential between the top of the drawtube and the bottom of the drawtube, and a controller connected to the motor and the pressure sensor and configured to vary the pumping rate of at least one of the pumps of the fluidic system to vary the flow rate of the system fluid and induce a commensurate change in the pressure of the system fluid to create pulsations within the system fluid in response to detection of a clog that provides to unclog the flow channel of the flow cytometer.

5. The fluidic system of claim 1, wherein the clog detector comprises a flow meter that automatically detects clogs in the flow channel by measuring the flow rate of a sample fluid from a sample container into the interrogation zone.

6. The fluidic system of claim 1, wherein the pulsations unclog the flow channel of a substance in the flow channel.

7. The fluidic system of claim 6, wherein the substance is at least one of sample debris and clustered cells.

8. The fluidic system of claim 6, wherein the substance is in a portion of the flow channel before interrogation in the interrogation zone.

9. The fluidic system of claim 1, wherein the motor includes a variable drive ratio device and the sheath pump and the waste pump are driven by the motor, wherein the sheath pump and the waste pump may be operated at different pump speeds, wherein the controller is connected to the variable drive ratio device such that the controller can vary the pumping rates of the sheath pump and the waste pump.

10. The fluidic system of claim 1, further comprising at least one valve adapted to facilitate the control of the system fluid.

11. The fluidic system of claim 10, wherein the valve is a by-pass valve located near at least one of the pumps of the system, wherein the controller is operatively connected to the by-pass valve and is configured to divert a variable amount of the system fluid through the by-pass valve.

12. The fluidic system of claim 10, wherein the valve is a restrictive valve located near at least one of the pumps of the system, wherein the controller is operatively connected to the restrictive valve and is adapted to open and close the restrictive valve.

13. The fluidic system of claim 1, further comprising a second motor with second motor controls, wherein the sheath pump is driven by the first motor and the waste pump is driven by the second motor and wherein the sheath pump and the waste pump may be operated at different pump speeds, and wherein the controller is connected to at least one of the first motor controls and second motor controls such that the controller can vary the pumping rates of the sheath pump and the waste pump.

14. The fluidic system of claim 1, wherein the controller is further configured to terminate the creation of pulsations within the system fluid automatically once a pre-defined threshold for a parameter has been reached, wherein the pre-defined parameter is selected from the group consisting of a time interval, an energy output, a full return of flow, a partial return of flow, a break up of the clog, and combinations thereof.

15. The fluidic system of claim 1, wherein the controller is further configured to create pulsations in anticipation of a clog in the flow channel.

16. The fluidic system of claim 3, further comprising a drawtube that conveys a sample fluid from a sample container into the interrogation zone, wherein the pressure sensor measures a pressure differential between the top of the drawtube and the bottom of the drawtube.

17. The fluidic system of claim 4, wherein the pulsations unclog the flow channel of a substance in the flow channel.

18. The fluidic system of claim 17, wherein the substance is at least one of sample debris and clustered cells.

19. The fluidic system of claim 18, wherein the substance is in a portion of the flow channel before interrogation in the interrogation zone.

20. The fluidic system of claim 4, further comprising at least one valve adapted to facilitate the control of the system fluid.

21. The fluidic system of claim 20, wherein the valve is at least one of:

a by-pass valve located near at least one of the pumps of the system, wherein the controller is operatively connected to the by-pass valve and is configured to divert a variable amount of the system fluid through the by-pass valve; and a restrictive valve located near at least one of the pumps of the system, wherein the controller is operatively connected to the restrictive valve and is adapted to open and close the restrictive valve.

22. The fluidic system of claim 4, wherein the controller is further configured to create pulsations in anticipation of a clog in the flow channel.

\* \* \* \* \*

UNITED STATES PATENT AND TRADEMARK OFFICE
CERTIFICATE OF CORRECTION

| | | |
|---|---|---|
| PATENT NO. | : 8,262,990 B2 | Page 1 of 1 |
| APPLICATION NO. | : 12/857405 | |
| DATED | : September 11, 2012 | |
| INVENTOR(S) | : Nathaniel C. Bair and Collin A. Rich | |

It is certified that error appears in the above-identified patent and that said Letters Patent is hereby corrected as shown below:

Column 8, line 48, add claim 23:

"23. The fluidic system of Claim 1, further comprising a flow meter that automatically detects clogs in the flow channel by measuring the flow rate of a sample fluid from a sample container into the interrogation zone."

Signed and Sealed this
Thirtieth Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,262,990 B2
APPLICATION NO. : 12/857405
DATED : September 11, 2012
INVENTOR(S) : Nathaniel C. Bair and Collin A. Rich It is certified that error appears in the above-identified patent and that said Letters Patent is hereby corrected as shown below:

Delete the title page and substitute therefore the attached title page showing the corrected number of claims in patent.

Column 8, line 48, add claim 23:

"23. The fluidic system of Claim 1, further comprising a flow meter that automatically detects clogs in the flow channel by measuring the flow rate of a sample fluid from a sample container into the interrogation zone."

This certificate supersedes the Certificate of Correction issued October 30, 2012.

Signed and Sealed this
Fourth Day of December, 2012

David J. Kappos
*Director of the United States Patent and Trademark Office*

United States Patent
Bair et al.

(12)

(10) Patent No.: US 8,262,990 B2
(45) Date of Patent: *Sep. 11, 2012

(54) FLOW CYTOMETER SYSTEM WITH UNCLOGGING FEATURE

(75) Inventors: Nathaniel C. Bair, Ann Arbor, MI (US); Collin A. Rich, Ypsilanti, MI (US)

(73) Assignee: Accuri Cytometers, Inc., Ann Arbor, MI (US)

(*) Notice: Subject to any disclaimer, the term of this patent is extended or adjusted under 35 U.S.C. 154(b) by 102 days.

This patent is subject to a terminal disclaimer.

(21) Appl. No.: 12/857,405

(22) Filed: Aug. 16, 2010

(65) Prior Publication Data

US 2010/0319786 A1 Dec. 23, 2010

Related U.S. Application Data

(63) Continuation of application No. 11/735,456, filed on Apr. 14, 2007, now Pat. No. 7,780,916, which is a continuation-in-part of application No. 11/370,714, filed on Mar. 8, 2006, now Pat. No. 8,017,402.

(60) Provisional application No. 60/792,536, filed on Apr. 17, 2006.

(51) Int. Cl.
*G01N 21/00* (2006.01)
*B08B 7/00* (2006.01)
*F17D 1/00* (2006.01)
*G01N 35/08* (2006.01)

(52) U.S. Cl. ............ 422/62; 422/67; 422/68.1; 422/81; 422/500; 422/501; 137/7; 137/12; 137/15.01; 137/565.11; 436/50; 436/52

(58) Field of Classification Search .................. None
See application file for complete search history.

(56) References Cited

U.S. PATENT DOCUMENTS

| | | |
|---|---|---|
| 3,347,273 A | 10/1967 | Russell |
| 3,061,128 A | 12/1968 | Hakim |
| 3,672,402 A | 6/1972 | Bloemer |
| 4,112,735 A | 9/1978 | McKnight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |

(Continued)

FOREIGN PATENT DOCUMENTS

EP 466490 A 1/1992

(Continued)

*Primary Examiner* — Neil N Turk
(74) *Attorney, Agent, or Firm* — Jeffrey Schox

(57) ABSTRACT

The fluidic system with an unclogging feature of the preferred embodiment includes a flow channel, a sheath pump to pump sheath fluid from a sheath container into an interrogation zone, and a waste pump to pump waste fluid from the interrogation zone into a waste container. The sheath pump and/or the waste pump draw sample fluid from a sample container into the interrogation zone. The fluidic system also includes a controller to adjust the flow rate of the sample fluid from the sample container into the interrogation zone. The pump and controller cooperate to propagate a pulsation through the flow channel from the pump if the flow channel is clogged. The fluidic system is preferably incorporated into a flow cytometer with a flow cell that includes the interrogation zone.

23 Claims, 1 Drawing Sheet